United States Patent [19]

Schmidt et al.

[11] Patent Number: 4,727,109

[45] Date of Patent: Feb. 23, 1988

[54] PHARMACEUTICAL PREPARATION WITH AN ACTIVE SUBSTANCE OF LOW SOLUBILITY IN WATER AND GASTRIC JUICES

[75] Inventors: Peter C. Schmidt, Marburg; Bernd Stockebrand, Monchen-Gladbach; Gerhard Fischer, Eberbach, all of Fed. Rep. of Germany

[73] Assignee: R. P. Scherer Corporation, Troy, Mich.

[21] Appl. No.: 814,483

[22] Filed: Dec. 30, 1985

[30] Foreign Application Priority Data

Jan. 4, 1985 [DE] Fed. Rep. of Germany ....... 3500103

[51] Int. Cl.$^4$ .......................... A61K 9/00; A61K 9/66
[52] U.S. Cl. ..................... 424/455; 424/456; 514/781; 514/786; 514/789
[58] Field of Search .................. 424/20, 37, 38, 455, 424/456; 514/781, 789, 786

[56] References Cited

U.S. PATENT DOCUMENTS

| | | | |
|---|---|---|---|
| 3,197,369 | 7/1965 | Widmann et al. | 424/37 |
| 4,177,254 | 12/1979 | Khan et al. | 427/3 |
| 4,198,391 | 4/1980 | Grainger | 424/37 |
| 4,572,833 | 2/1986 | Pedersen et al. | 424/20 |
| 4,574,080 | 3/1986 | Roswall et al. | 424/33 |
| 4,595,583 | 6/1986 | Eckenhoff et al. | 604/890 |
| 4,605,548 | 8/1986 | Ushiyama et al. | 424/20 |

FOREIGN PATENT DOCUMENTS

1242547 8/1971 United Kingdom .
1590864 6/1981 United Kingdom .

Primary Examiner—Ronald W. Griffin
Attorney, Agent, or Firm—Keil & Weinkauf

[57] ABSTRACT

A pharmaceutical preparation having an active substance of low solubility in water and gastric juices that has an initially liquid carrier system consisting of a hydrophilic component, a hydrophobic component and a solubilizer. The solvent mixture contains 9 to 90 parts by weight of solubilizer and 90 to 5 parts by weight of a hydropholic component, such as polyethylene glykol, 1,2-propylene glykol, 1,3-butanediol, 1,4-butanediol, 1,2-propanediol, glycerol, mannitol, sorbitol or polyoxyethylene polyoxypropylene copolymerisate or mixtures of such substances, and 40 to 1 parts by weight of an oleophilic component, such as natural and/or semi-synthetic vegetable or animal oils or synthetic oils, such as neutral oil or waxes. The active substance is dissolved in the carrier system or dispersed in a stable way and for an oral application, is filled into drug capsules made of gelatine. In order to achieve a delayed release of the active substance (delayed-action effect), an adjuvant that is soluble in the carrier system is also added to the carrier system in the amount of up to 10 parts by weight, preferably 2 to 5 parts by weight that, after the dissolving of the capsule wall, develops in contact with the gastric juices a renewing permeable membrane. Suitable adjuvants are ethylcellulose, cellulose acetate phthalate, hydroxypropylmethylcellulose phthalate and vinylacetate crotonic acid copolymers or mixtures thereof.

8 Claims, 7 Drawing Figures

Milchsäureethylester / Polyethylenglykol 6000 / Miglyol 818

Fig. 6

Solketal / 1,3 Butandiol / Miglyol 810

PHARMACEUTICAL PREPARATION WITH AN ACTIVE SUBSTANCE OF LOW SOLUBILITY IN WATER AND GASTRIC JUICES

This invention relates to a carrier system for active substances of low solubility in water and gastric juices that, on the one hand, results in an especially advantageous biological availability of the active substances in the gastro-intestinal tract and, on the other hand, results by means of the addition of certain adjuvant substances in a delayed-action drug effect caused by a time-delayed release of the substance.

Liquid carrier systems for pharmaceutical preparations that for oral administration are filled into drug capsules are known principle. In GB-PS 1 590 864, an inert carrier system is described that in liquid or pasty form can be filled into hard gelatine capsules. Used as the carrier material are vegetable oils, animal fats or oils and semisynthetic and synthetic oils to which additional adjuvant substances may be added in order to give the mixture thioxtrope characteristics.

From the European Patent Application No. 78 10 1259, a liquid carrier system is known in the form of a water-soluble melt mass having a solidification point of between 30° and 60° or a thixotrope gel. The liquid carrier is a polyethylene glycol or a mixture of such glycols having a molecular weight in the range of 1,000 to 6,000. As a thixotrope gelling agent hydrogenated castor oil is described among other things. The carrier system may in addition also contain paraffin oil.

Oral delayed-action drugs continuously release the stored active substance over a period of six to eight hours. They facilitate the medicating by, being taken as a rule in the morning and in the evening, ensuring a steady blood level appropriate with respect to the therapy. The development of delayed-action drugs, for about 15 years, has been in the center of pharmaceutical-technological research. Thus, delayed-action drugs are manufactured in very different ways as tablets and coated pills. Ion exchangers and pellets are preferably filled into insertion capsules made of gelatine (hardgelatine capsules).

Microcapsules having semipermeable walls are known from which the active substances are released in a time-delayed manner. However, microcapsules of this type are not suitable for the oral administration of medications because the required dosing precision of the microcapsules to be taken cannot be achieved without additional aids, such as filling the microcapsules into larger coverings.

Delayed-action drugs in the form of a soft-gelatine capsule are known from DE-AS No. 16 17 845. The principle of the delayed-action effect is based on the fact that the liquid content of the capsule, because of the presence of physiologically indifferent natural and/or synthetic substances that remain undissolved for a sufficiently long time in water or the gastric juices of the gastro-intestinal tract, when it comes in contact with this medium, forms a sponge-type shaped body from which the medication is released slowly by diffusion. The carrier system that is used for this pharmaceutical preparation consists of one or several physiologically indifferent natural and/or plastic substances that are dissolved or suspended in a suitable carrier medium, as liquid components, polyethylene glycols, dioxalanes, liquid alcohols, oils or fats that are water-soluble or can be mixed with water being described as suitable components.

This carrier system, however, has disadvantages. It was found that the active substances are not always released from the shaped body in the desired way. The diffusion paths for the medication increase constantly so that after four to five hours, there is no longer any significant release of the medication.

It is the objective of this invention to provide a carrier system for active substances of low solubility in water and gastric juices in which the active substances can be dissolved or dispersed in a stable way so that the active substances, when they are administered orally, after the dissolving of a protective cover, are present in the gastro-intestinal tract in a form in which they are biologically available in a particularly advantageous way.

This objective is achieved by means of the pharmaceutical preparation according to claim 1.

Preferred embodiments of the invention are described in the subclaims.

The carrier system is a homogenous liquid-liquid and consists of a hydrophobic component, a hydrophilic component and a solubilizer in such amounts that a homogeneous phase is present.

The selection of the amounts of the components for reaching the homogeneous phase can easily take place from mixing diagrams of the three components in which the homogeneous and the heterogeneous range is indicated. These mixing diagrams can be established on the basis of mixing tests in the trilinear coordinate system.

The initially liquid carrier system preferably dissolves the active substance or substances so that these are optimally available biologically.

The hydrophilic component of the carrier system consists of hydrophilic liquid or pasty substances, such as polyethylene glycol of molecular weights of 200 to 6,000, 1,2-propylene glycol, 1,3-butanediol, 1,4-butanediol, 1,2-propanediol, polyoxyethylenepolyoxypropylene copolymerisates, glycerol, mannitol, sorbitol and other polyhydric alcohols as well as mixtures of these substances. It is important that these substances, in addition to hydrophylic parts in the molecule, also contain a hydrophobic molecule component.

As a rule, the substances cannot be mixed with vegetable or animal oils, semisynthetic or synthetic oils or waxes that act hydrophobically. By means of the addition of a solubilizer, however, as shown, for example, in FIG. 1 for the poylethylene glycol system (molecular weight 400) with respect to castor oil and triethylcitrate, when certain limits are observed, a monophase liquid mixture can be produced in which active substances of low solubility in water can be dissolved especially well or can be dispersed in it in a stable and fine-particled way. The solvent characteristics of the mixture, by means of an increase of the hydrophilic component and a decrease of the hydrophobic component or the reversed increase and decrease, can be especially well adapted to the special requirements of the active substances. Triethylcitrate in this case is an essential component of the mixture so that it is ensured that a monophase liquid carrier system is developed.

The suitable hydrophobic component are natural or partially synthetic or synthetic vegetable oils, particularly liquid seed fat, such as rapeseed oil, sunflower seed oil, sesame seed oil, soy oil, castor oil, penaut oil, olive oil, wheat germ oil, cotton seed oil, linseed oil, rapeseed oil (sic) or other, also partially synthetic oils. Also suitable are animal fats, such as fish oil, cod liver oil and others. However, neutral oils are also suitable, such as saturated triglyceride, the fatty acids of which have chain lengths of C8 to C18. Oils of this type are offered under the trade name of Miglyol. However, several waxes may also be used, such as oleic acid oleylesters or isopropylmyristate.

Suitable as solubilizers for the hydrophilic/hydrophobic mixture are 2,2-dimethyl-4-hydroxymethyl-1,3-dioxolane, triacetin (glycerine triacetate), triethylcitrate, tributylcitrate, acetyltributylcitrate, acetyltriethylcitrate, lactic acid ethylesters, tetrahydrofurfurylalcohol or mixtures of these substances. Triethylcitrate, tributylcitrate and triacetin are especially preferred.

Active substances in amounts of 0.1 to 70 percent in weight relative to the total amount can be added to such a liquid carrier system.

Very surprisingly, it was found that this carrier system may also be changed for the development of a delayed-action effect by adding adjuvant substances that in the gastro-intestinal tract cause the formation of a membrane around liquid drops of the carrier system. By means of the addition of up to 10 parts by weight, preferably two to five parts by weight of such an adjuvant substance, such as ethyl cellulose, cellulose acetate phthalate, hydroxypropylmethylcellulose phthalate, vinylacetate crotonic acid copolymers or a mixture of these substances, it is achieved that after the dissolving of a protective cover that permits an oral administration of the pharmaceutic preparation, a constantly regenerating membrane is formed around the drop of liquid. This membrane formation results in a delayed release of the active substance so that the desired delayed-action drug effect is achieved.

The above-mentioned adjuvant substances dissolve in the carrier fluid and at contact with the aqueous gastric juices form a permeable membrane that continuously renews itself by means of the membrane material resupplied out of the interior of the liquid drop. In this way, a shaped body formed from the liquid drop changes its shape while continuously developing fresh permeable membranes during the whole release process of the active substance. For example, in the case of a high loading with medication of the composition, when the active substance is separated, ducts and pores will appear in the developed membrane film, for example, made of ethylcellulose. However, these ducts and pores are closed again by means of ethylcellulose located in the interior of the shaped body. The permeability of the membrane can be adapted according to the active substance and can be adjusted by means of the proportion of the hydrophilic component in the carrier system. The combination of ethylcellulose as a suitable adjuvant substance with a hydrophilic component and an oil, such as citric triethylester in certain quantitative proportions results in the formation of a dimensionally stable gel already inside the drug capsules and to the later formation of membranes that renew themselves out of the cellulose derivative when coming in contact with the medium of the gastro-intestinal tract after the dissolving of the wall of the drug capsule.

The combination of the carrier system according to the invention with another adjuvant substance results in the formation of a shaped body already in the drug capsules. It is therefore possible to fill the initially liquid pharmaceutical preparation not only into soft-gelatine capsules but also into the known insertion capsules made of hard gelatine without the requirement of special sealing measures at the individual capsules. After the dissolving of the gelatine cover, the shaped body, in contact with the aqueous gastric juices, will then develop a membrane that permits a diffusion of the active substance.

The pharmaceutical preparation may also contain the adjuvant substances conventionally used in the manufacturing of drug capsules that provide consistency or increase the sliding ability in the capsule machines, such as fine-particled silicon dioxide, lecithin, phosphates, acids, bases and buffer substances, in which case, however, such adjuvant substances are preferred that are dissolved by the monophase carrier liquid. Insoluble substances, such as fine-particled silicon dioxide, are added to the carrier system in only small quantities in order to promote the gel formation already in the drug capsule.

The carrier system according to the invention may, however, also be developed without the delayed active-substance release (delayed-action effect) because, as a result of the adjustability of the dissolution effect, it is an especially good solvent for active substances of low solubility in water and gastric juices. The adaptation of the dissolution characteristics to the requirements of special active substances, as described, takes place by changing the mixture ratio of the hydrophobic component, the hydrophilic component and of the solubilizer. From this carrier system, the active substances are particularly well biologically available and can be absorbed by the body although they are active substances that are hard to dissolve in the gastric juices.

In the case of the conventional drug capsules made of gelatine that contain delayed-action drugs, the release usually starts about 5 minutes after application. The release rates, by means of the adjustment of the permeability of the membrane and the substance composition of the membrane, can be adapted to the diffusion speed of the active substance in such a way that the release is distributed evenly over a period of one to eight hours. Preferably, the adjusting of the permeability takes place in such a way that six hours of the administration of the capsule, about 70 to 90% of the active substance are released.

As active substances for the carrier system according to the invention, those substances can be used that are soluble in the liquid composition and can be dispersed or emulsified in a stable way, in which case active substances that are hard to dissolve in water and gastric juices are preferred. Active substances for which a delayed-action effect is not required or desirable are, for example,

| | |
|---|---|
| alkaloids | dehydroergocristin methane sulfonate |
| | dehydroergotoxin methane sulfonate |
| | noscapine |
| | reserpine |
| antirheumatics | indomethacin |
| | ibuprofen |
| antidiabetics | glibenclamide |
| benzodiazepines | diazepam |
| | bromazepam |
| glucocorticoids | dexamethasone |
| | prednisolone |
| diuretics | furosemide |
| | hydrochlorothiazide |
| | spironolactone |
| circulatory aids | benzaron |
| tricyclic psychopharmaceutical | carbamazepin |

-continued substances

Examples of active substances for which a delayed-action effect may be adjusted:

antitussive alkaloids, such as codeine, dihydrocodeine, ethylmorphine;

xanthine derivatives, such as theophylline, proxyphylline, diprophylline, coffeine;

antirheumatics, such as indomethacin, dichlophenac and other known antiinflammatory active substances;

β-receptor blockers, such as pindolol HCl, propanolol HCl;

antihypetonics, such as etilefrin HCl;

but also nifedipin.

The invention will now be explained in detail by means of several selected examples.

EXAMPLE 1

Figure 1:
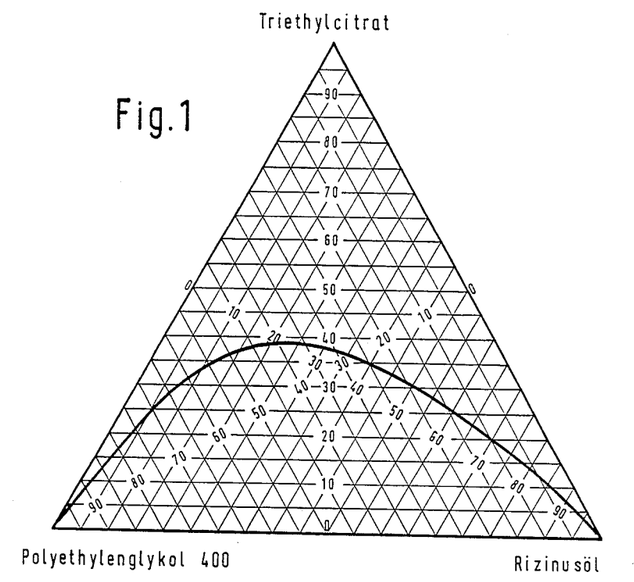

This example relates to the polyethylene glycol 400-castor oil-triethylcitrate system. The mixture diagram is shown in FIG. 1. The area above the curve shows the field of the homogeneous liquid-liquid; the area below the curve shows an undesirable polyphase carrier system. The diagram shows that especially 1 to 40 parts by weight of the hydrophobic component, in this case castor oil, result in a homogenous phase with the two other components. When at least 5 parts by weight of polyethylene glycol are present, about 10 parts by weight triethylcitrate are sufficient as the solubilizer in order to, with about 85 parts by weight of castor oil, still form a homogeneous phase. However, for practical purposes, the proportion of the hydrophobic component should not be above 40 parts by weight because at higher proportions, the dissolving capacity of the carrier system for the active substances is reduced. The upper limit for the hydrophilic component is at about 90 parts by weight, in which case, with rising contents of the hydrophobic component, the required amount of solubilizer also increases in order to form a homogeneous phase.

EXAMPLE 2

Figure 2:
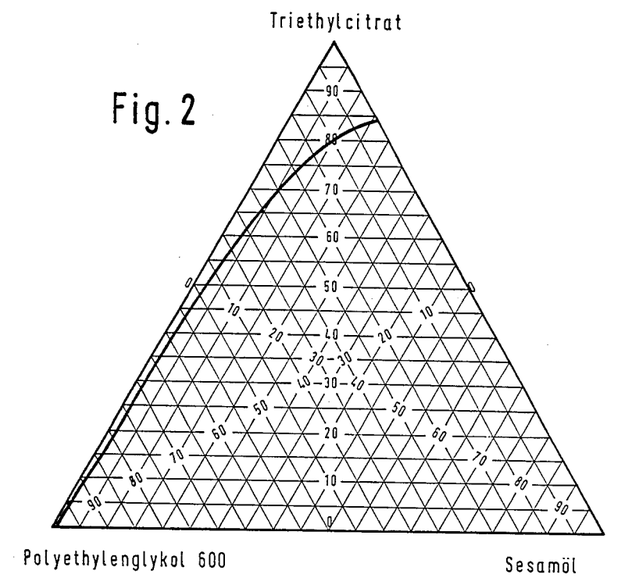

This example relates to the polyethylene glycol 600-sesame oil-triethylcitrate system. The mixture diagram shown in FIG. 2 demonstrates that, when sesame oil is used as the hydrophilic component, its proportion must not be about 10 parts by weight. In the case of higher proportions than 5 parts by weight of polyethylene glycol, the proportion of the hydrophobic component in the case of sesame oil should be chosen to be still lower. In this system, high proportions of solubilizer are preferred.

Figure 3:
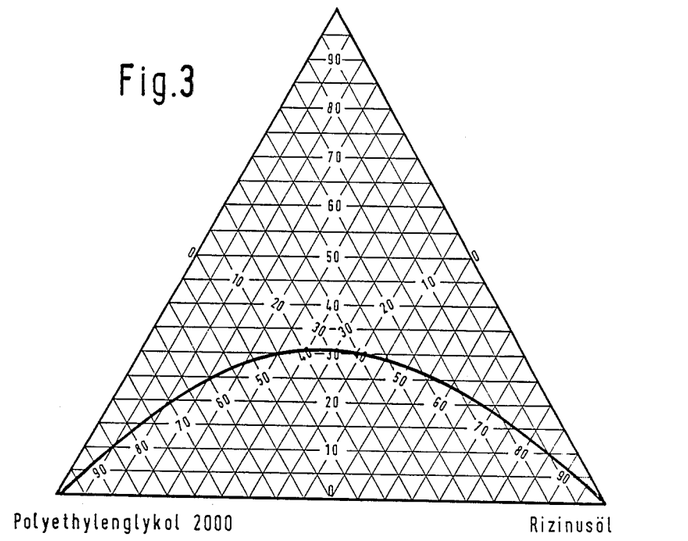

EXAMPLE 3 describes the polyethylene glycol 2000-castor oil-solketal (2,2-dimethyl-4-hydroxymethyl-1,3-dioxolan) system that, as shown in FIG. 3, results in a wide range of mixtures with a homogeneous phase. The area located above the curve represents the filed of the homogeneous phase. Nevertheless, it is preferred to limit the proportion of hydrophobic component to about 40 parts by weight.

Figure 4:
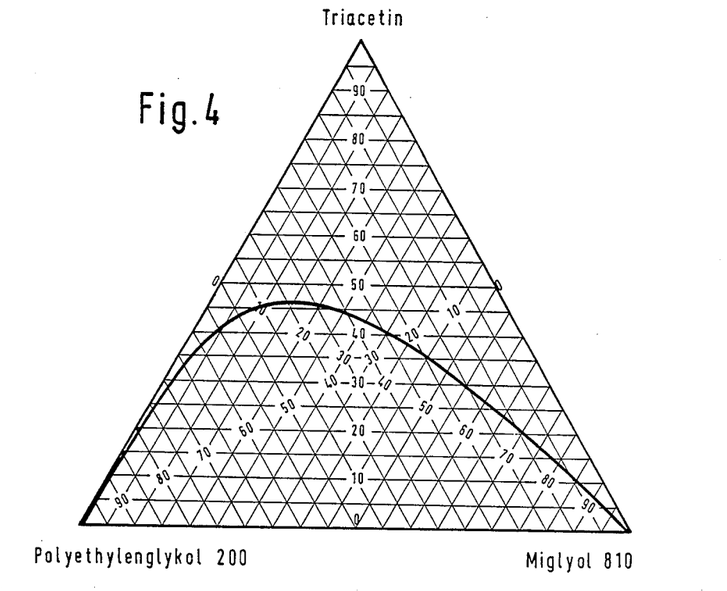

EXAMPLE 4 relates to the polyethylene glycol 200-miglyol 810-triacetin system. FIG. 4 shows the mixture diagram with the area of the homogeneous phase located above the curve. Even relatively low proportions of hydrophobic component require 35 and more parts by weight solubilizer for achieving a homogeneous phase. This example shows especially clearly that the solubilizer is of considerable importance in the carrier system.

Figure 5:
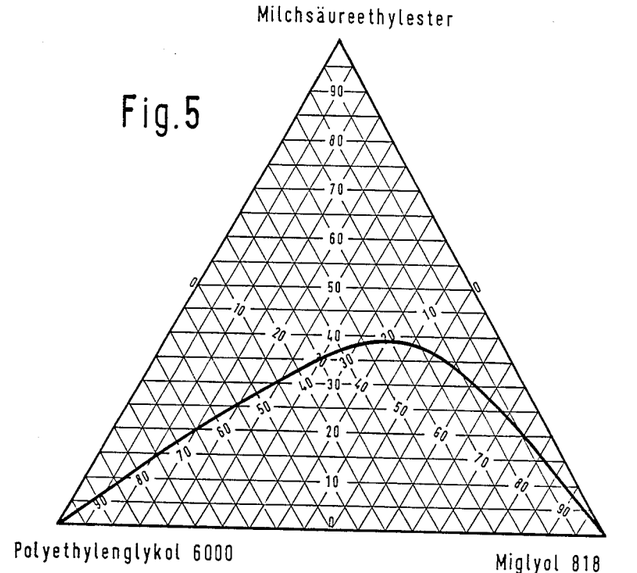

EXAMPLE 5 relates to the polyethylene glycol 6000-miglyol 818-lactic acid ethylester system. The mixture diagram of FIG. 5 shows that also higher-molecule polyethylene glycol together with the hydrophobic component by means of the solubilizer can be mixed over a wide range to a homogeneous phase.

Figure 6:
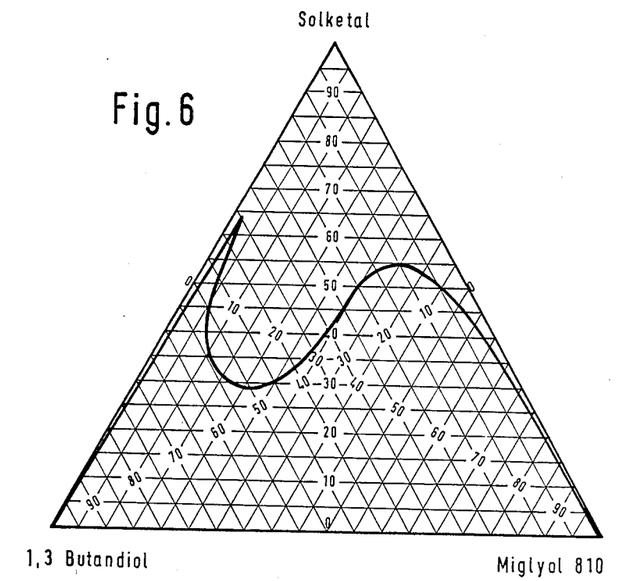

EXAMPLE 6 relates to the 1,3 butanediol-miglyol 810-solketal system. The mixture diagram in FIG. 6 deviates slightly from the diagrams of the preceding examples because there is a range in the homogeneous phase at proportions of about 5 to about 40 parts per weight of hydrophobic component where the proportion of the solubilizer may be below 50 parts by weight so that a high proportion of hydrophobic component is possible. In this case also, the homogeneous area is above the curve.

Figure 7:
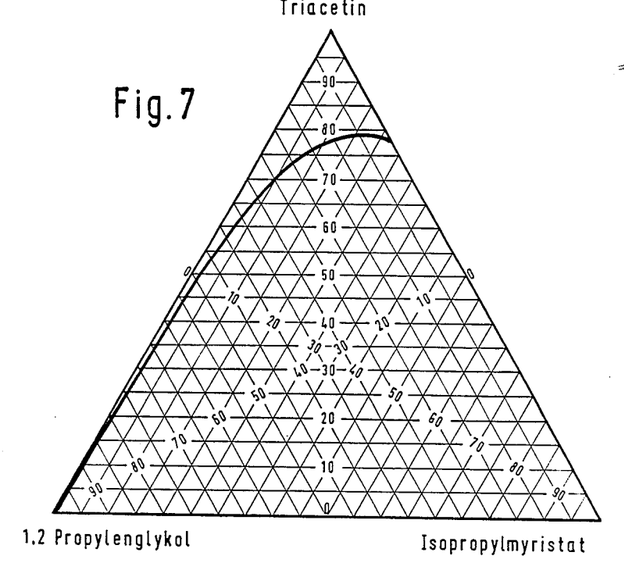

EXAMPLE 7 at the 1,2 propylene glycol-triacetin-isopropylmyristate system, show the suitability of selected waxes as the hydrophobic component of the carrier system. FIG. 7 shows the mixture diagram which indicates that only up to 15 parts by weight of isopropylmyristate may be used when a high proportion of solubilizer (about 80 parts by weight) is present. In this system, high proportions of solubilizer are required, in which case, however, the other components contribute sufficiently to the solubility of the active substances also at lower concentrations.

EXAMPLE 8

In order to demonstrate the particularly good dissolving characteristics of the carrier system according to the invention, for different active substances, the following three mixtures were selected from Examples 1, 3 and 4:

"Mixture No. 1": from the three-phase diagram Example 1, the following mixture was selected:

| polyethylene glycol 400 | 45 percent in weight |
|---|---|
| triethylcitrate | 45 percent in weight |
| castor oil | 15 percent in weight |

"Mixture No. 2": from the three-phase diagram Example 3, the following mixture was selected:

| polyethylene glycol 2000 | 40 percent in weight |
|---|---|
| solketal | 50 percent in weight |
| castor oil | 10 percent in weight |

"Mixture No. 3": from the three-phase diagram Example 4, the following mixture was selected:

| polyethylene glycol 200 | 35 percent in weight |
|---|---|
| triacetin | 50 percent in weight |
| miglyol 810 | 15 percent in weight |

In these three mixtures of the carrier system according to the invention, the dissolving behavior of several active substances was determined in the conventional dosages for drug capsules. The following table, for each of the active substances, shows the amount that was dissolved in an indicated amount of the carrier system. The second to the last column shows the resulting total amount of the pharmaceutical preparation. The last column indicates in which of the mixtures the active substance was completely soluble when heated slightly under the indicated conditions.

or suspending of the codeine in the mixture, the filling of the capsule takes place on a conventional soft-capsule filling machine. In this case, the filling weights are such that each capsule contains 30 mg of codeine.

Release Methods

1. Half-Change Method according to NF 14 with the following deviations:
Number of revolutions of the star wheel 28 min$^{-1}$
Testing volume 100 ml
Testing media:

| Class of Drugs | Example | Amount of Dissolved Active Substance (mg) per Capsule | Amount of Carrier System (mg) per Capsule | Total Weight of the Capsule Filling (mg) | No. of Mixture to Be Dissolved |
|---|---|---|---|---|---|
| Alkaloids | dehydroergocristin methane sulfonate | 1 | 500 | 501 | 1,2,3 |
|  | dehydroergotoxin methane sulfonate | 1 | 500 | 501 | 1,2,3 |
|  | noscapine | 25 | 500 | 525 | 2,3 |
|  | reserpine | 0.1 | 500 | 500.1 | 1,2,3 |
| Antirheumatics | indomethacin | 50 | 500 | 550 | 1,2,3 |
|  | ibuprofen | 200 | 1,000 | 1,200 | 1 |
| Antidiabetics | glibenclamide | 3.5 | 500 | 503.5 | 1,3 |
| Benzodiazepines | diazepam | 5 | 500 | 505 | 1,2,3 |
|  | bromazepam | 6 | 500 | 506 | 1,3 |
| Glucocorticoids | dexamethasone | 0.5 | 500 | 500.5 | 1,2,3 |
|  | prednisolone | 2 | 500 | 502 | 1,2,3 |
| Diuretics | furosemide | 20 | 500 | 520 | 1,2,3 |
|  | hydrochlorothiazide | 25 | 500 | 525 | 1,2 |
|  | spironolactone | 25 | 500 | 525 | 2,3 |
| Circulatory aids | benzaron | 100 | 1,000 | 1,100 | 1,2,3 |
| Tricyclic psychopharmaceutical substances | carbamazepin | 100 | 1,000 | 1,100 | 2 |

EXAMPLE 9

| | Codeine as an Active Substance in the Carrier System 1. Codeine Preparations | | | | | | | | | |
|---|---|---|---|---|---|---|---|---|---|---|
| | VA1 | VA2 | VA3 | VA4 | VA5 | VA6 | VA7 | VA8 | VA9 | % in Weight |
| Ethylcellulose$^{(x)}$ | 4.0 | 3.0 | 3.0 | 3.5 | 3.5 | 5.0 | 10.0 | 2.0 | 5.0 | % in weight |
| PEG 400 | 27.5 | 20.0 | 22.0 | 20.0 | — | 20.0 | — | 20.0 | 20.0 | % in weight |
| PEG 600 | — | — | — | — | 20.0 | — | — | — | — | % in weight |
| Sesame oil | 9.0 | 10.0 | 10.0 | 10.0 | 10.0 | 10.0 | — | 10.0 | 10.0 | % in weight |
| Triethylcitrate | 59.5 | 67.0 | 65.0 | 66.5 | 66.5 | 65.0 | 63.0 | 68.0 | 65.0 | % in weight |
| Neutral oil | — | — | — | — | — | — | 27.0 | — | — | % in weight |
| Active substance dissolved or suspended (g/s) | g | g | g | g | g | g | g | s | s | |
| Weight of the carrier system per capsule | 230 | 230 | 230 | 230 | 230 | 270 | 270 | 170 | 170 | mg |

$^{(x)}$commercial product with a nominal viscosity of 20 mPas in toluol/ethanol at 25° C., 5% solution, ethoxyl content 47–49.5%.

Suitable ethylcelluloses for producing the delayed-action effect for all active substances have a nominal viscosity of 10–300 m/Pas, preferably 10 to 20 or 50 mPas in the mentioned solvent mixture.

Ethylcellulose is dissolved in the mixture of triethylcitrate and sesame oil or neutral oil in heat; the polyethyleneglycol is added and mixed. After the dissolving artificial gastric juice (stomach) USP XX, without enzymes, pH 1.20 artificial gastric juice (intestine) USP XX, without enzymes, pH 7.50

2. Paddle Method USP XX
Number of revolutions always 100 min$^{-1}$
Testing medium for codeine preparations: dist. water Results

| 1. Codeine Preparations (Half Change) | | | | |
|---|---|---|---|---|
| VA 1 | VA 2 | VA 3 | VA 4 | VA 5 |

-continued

| h | mg/h | % | mg/h | % | mg/h | % | mg/h | % | mg/h | % |
|---|------|---|------|---|------|---|------|---|------|---|
| 1 | 20.0 | 66.7 | 18.0 | 60.0 | 17.1 | 57.0 | 15.1 | 50.5 | 17.3 | 57.6 |
| 2 | 3.6 | 78.7 | 3.2 | 70.2 | 3.0 | 66.9 | 3.4 | 61.9 | 2.6 | 66.4 |
| 3 | 1.7 | 84.4 | 1.8 | 76.7 | 1.7 | 72.7 | 1.9 | 68.2 | 1.3 | 70.5 |
| 4 | 1.0 | 87.7 | 1.2 | 80.7 | 1.5 | 77.6 | 1.5 | 73.2 | 1.1 | 74.2 |
| 5 | 0.9 | 90.2 | 1.0 | 84.0 | 1.1 | 81.1 | 1.1 | 77.0 | 1.5 | 79.2 |
| 6 | 0.6 | 92.7 | 0.9 | 87.0 | 1.0 | 84.6 | 1.2 | 81.2 | 0.6 | 81.1 |

| | VA 6 | | VA 7 | | VA 8 | | VA 9 | |
|---|---|---|---|---|---|---|---|---|
| h | mg/h | % | mg/h | % | mg/h | % | mg/h | % |
| 1 | 14.9 | 49.7 | 10.2 | 34.0 | 15.7 | 52.5 | 13.3 | 44.4 |
| 2 | 2.0 | 56.4 | 4.6 | 49.2 | 4.2 | 66.5 | 3.2 | 55.1 |
| 3 | 1.4 | 61.0 | 3.1 | 59.7 | 2.7 | 75.4 | 2.4 | 63.0 |
| 4 | 1.2 | 65.0 | 2.2 | 66.9 | 1.8 | 81.5 | 1.6 | 68.3 |
| 5 | 0.8 | 67.7 | 1.8 | 72.7 | 0.9 | 84.6 | 1.5 | 73.2 |
| 6 | 0.7 | 70.9 | 1.3 | 77.0 | 0.6 | 86.6 | 1.2 | 77.1 |

2. Codeine Preparations (Paddle)

| | VA 6 | | VA 7 | | VA 8 | | VA 9 | |
|---|---|---|---|---|---|---|---|---|
| h | mg/h | % | mg/h | % | mg/h | % | mg/h | % |
| 1 | 12.8 | 42.7 | 9.5 | 31.8 | 9.7 | 32.3 | 8.1 | 26.9 |
| 2 | 3.7 | 55.1 | 5.4 | 49.6 | 5.3 | 50.1 | 4.4 | 41.4 |
| 3 | 2.5 | 63.3 | 3.8 | 62.4 | 3.3 | 60.9 | 3.2 | 52.0 |
| 4 | 1.8 | 69.3 | 3.0 | 72.4 | 3.4 | 72.3 | 2.5 | 60.3 |
| 5 | 1.3 | 73.6 | 2.4 | 80.2 | 2.6 | 81.0 | 2.2 | 67.5 |
| 6 | 1.1 | 77.0 | 1.7 | 85.3 | 1.9 | 87.4 | 1.7 | 73.0 |

The results show that by varying the recipe different release profiles can be obtained.

COMPARATIVE EXAMPLE 9

In order to demonstrate the superior effect of the carrier system according to the invention, the following comparison was made.

1. Soft-gelatine capsule according to Example 3 of DE-PS No. 16 17 845
2. commercial soft-gelatine capsule, with 35 mg of codeine per capsule (Longtussin) according to Example 4 of DE-PS 16 17 845
3. Example 5 of DE-PS 16 17 845

Codeine Release from recipes in the Half-Change Test as in Example 9:

| | Nr. 1 | | Nr. 2 | | Nr. 3 | |
|---|---|---|---|---|---|---|
| h | mg/h | % | mg/h | % | mg/h | % |
| 1 | 20.8 | 69.1 | 9.1 | 30.3 | 6.8 | 22.7 |
| 2 | 4.3 | 83.6 | 3.9 | 43.3 | 2.9 | 32.5 |
| 3 | 1.9 | 90.0 | 2.5 | 51.6 | 1.5 | 37.6 |
| 4 | 0.8 | 92.8 | 1.9 | 58.0 | 1.7 | 43.5 |
| 5 | 0.4 | 94.1 | 1.0 | 61.3 | 0.9 | 46.6 |
| 6 | — | — | 0.7 | 63.6 | 0.5 | 48.3 |

The comparison of Examples 9 demonstrates that the carrier system according to the invention contains and releases the active substance codeine with clearly higher biological availability.

EXAMPLE 10

Theophylline as an Active Substance

| 2. Theophylline Preparations | | | |
|---|---|---|---|
| | VA - T 1 | VA - T 2 | |
| Ethylcellulose(x) | 2.0 (20 caps.) | 2.0 (10 cps) | Percent in Weight |
| PEG 400 | 35.0 | 35.0 | Percent in Weight |
| Sesame oil | 5.0 | 5.0 | Percent in Weight |
| Triethylcitrate | 58.0 | 58.0 | Percent in Weight |

-continued

| 2. Theophylline Preparations | | |
|---|---|---|
| | VA - T 1 | VA - T 2 |
| Active substance suspended | | |

(x)Commercial quality with an ethoxyl content of 47–49.5% and a nominal viscosity of 20 mPas in toluol/ethanol at 25° C. in a 5% solution for VA-T1 and 10 mPas for VA-T2.

Production

The production takes place as indicated in Example 9. The filling weights are such that each capsule contains 300 mg of theophylline.

Release Methods

See Example 9, where, for determining the release according to the padding method, artificial gastric juice (stomach) was used in the first and second hour and artificial gastric juice (intestine) was used from the 3rd to the 7th hour, according to USP XX.

Release Results

3. Theophylline Preparations (Half-Change)

| | VA - T 1 | | VA - T 2 | |
|---|---|---|---|---|
| h | mg/h | % | mg/h | % |
| 1 | 95.0 | 31.7 | 118.8 | 39.6 |
| 2 | 28.6 | 41.2 | 54.0 | 57.6 |
| 3 | 21.0 | 48.2 | 38.1 | 70.3 |
| 4 | 13.9 | 52.9 | 24.6 | 78.5 |
| 5 | 20.3 | 59.6 | 38.1 | 91.2 |
| 6 | 16.3 | 65.1 | 15.9 | 96.5 |
| 7 | 11.6 | 69.0 | 7.2 | 98.9 |

4. Theophylline Preparations (Paddle)

| | VA - T 1 | | VA - T 2 | |
|---|---|---|---|---|
| h | mg/h | % | mg/h | % |
| 1 | 89.8 | 32.9 | 133.8 | 44.6 |
| 2 | 26.0 | 41.6 | 35.8 | 56.5 |
| 3 | 17.9 | 47.6 | 47.3 | 72.3 |
| 4 | 24.3 | 55.7 | 37.3 | 84.7 |
| 5 | 22.5 | 63.2 | 17.7 | 90.6 |
| 6 | 22.0 | 70.5 | 17.2 | 96.4 |

| 7 | 11.2 | 75.3 | 1.0 | 96.7 |

EXAMPLE 11

Indomethacin as an Active Substance

Recipes for Indomethacin

|  | 1 | 2 | 3 | |
|---|---|---|---|---|
| Ethylcellulose | 2 | 1 | 1 | % in weight |
| Cellulose acetate phthalate | 2 | 3 | 5 | " |
| PEG 400 | 35 | — | — | " |
| Propylene glycol | — | 35 | 40 | " |
| Sesame oil | 10 | — | — | " |
| Miglyol 812 | — | 10 | 10 | " |
| Triethylcitrate | 51 | 51 | 49 | " |
| Weight of the carrier system per capsule | 150 | 150 | 150 | mg |
| Indomethacin per capsule | 75 | 75 | 75 | mg |

Release results of the indomethacin recipes (Paddle Method) as in Example 9; however, pH 7.5

|  | 1 | 2 | 3 | |
|---|---|---|---|---|
| Ethyl cellulose | 3.6 | 3.1 | 3.6 | % in weight |
| PEG 400 | 20 | 17.6 | — | " |
| Propylene glycol | — | — | 20 | " |
| Sesame oil | 10 | 8.8 | 10 | " |
| Triethylcitrate | 66.4 | 58.5 | 66.4 | " |
| Weight of the carrier system per capsule | 270 | 320 | 225 | mg |
| Active substance per capsule | 30 | 80 | 25 | mg |

The release rates of the carrier system to which the delayed-action effect was added show the high biological availability of the active substance in the period of 6 hours after oral application when the pharmaceutical composition for the oral application is filled into soft-gelatine capsules.

EXAMPLE 12

Active Substances: Pindolol HCl (No. 1), Propanolol HCl (No. 2) and Etilefrin HCl (No. 3)

| h | 1 | | 2 | | 3 | |
|---|---|---|---|---|---|---|
|  | mg/h | % | mg/h | % | mg/h | % |
| 1 | 18.5 | 24.7 | 20.3 | 27.1 | 25.0 | 30.0 |
| 2 | 8.0 | 33.3 | 9.3 | 39.5 | 9.5 | 46.0 |
| 3 | 4.5 | 41.3 | 5.1 | 46.3 | 6.9 | 55.2 |
| 4 | 5.1 | 48.1 | 4.9 | 52.8 | 5.0 | 61.9 |
| 5 | 4.7 | 54.4 | 5.3 | 55.9 | 5.5 | 69.3 |
| 6 | 4.8 | 60.8 | 4.5 | 61.9 | 4.9 | 75.7 |

Release results pindolol HCl (1), propanolol HCl (2) and etilefrin HCl (3). (Paddle Method, 0.1N HCl)

| h | 1 | | 2 | | 3 | |
|---|---|---|---|---|---|---|
|  | mg/h | % | mg/h | % | mg/h | % |
| 1 | 5.3 | 17.7 | 16.2 | 20.3 | 7.9 | 31.6 |
| 2 | 2.4 | 25.7 | 17.6 | 42.3 | 1.3 | 36.6 |
| 3 | 2.3 | 33.4 | 26.0 | 74.8 | 1.1 | 41.1 |
| 4 | 2.6 | 41.9 | 2.2 | 77.5 | 1.2 | 45.7 |
| 5 | 2.3 | 49.7 | 1.0 | 78.7 | 1.6 | 52.1 |
| 6 | 2.0 | 56.1 | 1.2 | 80.2 | 1.0 | 55.9 |

We claim:

1. A pharmaceutical preparation containing an active substance of low solubility in water and gastric juices, in a solvent mixture, and adjuvants as the carrier system, wherein the solvent mixture is a homogeneous phase and contains 90 to 5 parts by weight of polyethylene glycol of mole weights of 200 to 6,000, 1,2-propylene glycol, 1,3-butanediol, 1,4-butanediol, 1,2-propanediol, glycerol, mannitol, sorbitol, polyoxyethylene polyoxypropylene copolymerisate or mixtures thereof, 40 to 1 parts by weight of natural and/or semisynthetic and/or synthetic oils and/or waxes and 9 to 90 parts by weight of a solubilizer or of a mixture of solubilizers.

2. A pharmaceutical preparation according to claim 1, wherein 2,2-dimethyl-4-hydroxymethyl-1,3-dioxolane, glycerine triacetate, triethylcitrate, tributylcitrate, acetyltributylcitrate, acetyltriethylcitrate, lactic acid ethylesters or tetrahydrofurfuryl alcohol are contained as solubilizers.

3. A pharmaceutical preparation according to claim 1 or 2, wherein the oil is a liquid seed fat, a liquid animal fat, a neutral oil or an oleic acid oleylester or an isopropylmyristate or a mixture thereof.

4. A pharmaceutical preparation according to claim 1 or 2, wherein the carrier system also contains 2 to 5 parts by weight of an adjuvant or adjuvants that is or are soluble in the carrier system.

5. A pharmaceutical preparation according to claim 4, wherein the adjuvant is ethylcellulose, cellulose acetate phthalate, hydroxypropylmethylcellulose phthalate, vinylacetate crotonic acid copolymers or a mixture thereof.

6. A pharmaceutical preparation according to claim 1 or 2, wherein the concentration of the active substance in the carrier system is 0.5–70% in weight relative to the total amount.

7. A pharmaceutical preparation according to claim 1 or 2, wherein it is filled into a drug capsule made of hard or soft gelatine.

8. A pharmaceutical preparation according to claim 7, wherein the dosage amount is 0.1 mg to 1 g active substance per drug capsule.

* * * * *